United States Patent
Gabl et al.

(10) Patent No.: US 7,988,351 B2
(45) Date of Patent: Aug. 2, 2011

(54) DEVICE COMPRISING A PIEZOELECTRIC RESONATOR ELEMENT, METHOD FOR PRODUCING THE SAME AND METHOD FOR OUTPUTTING A SIGNAL DEPENDING ON A RESONANT FREQUENCY

(75) Inventors: Reinhard Gabl, St. Peter im Sulmtal (AT); Matthias Schreiter, München (DE)

(73) Assignee: Siemens Aktiengesellschaft, Munich (DE)

( * ) Notice: Subject to any disclaimer, the term of this patent is extended or adjusted under 35 U.S.C. 154(b) by 596 days.

(21) Appl. No.: 12/066,084

(22) PCT Filed: Sep. 7, 2006

(86) PCT No.: PCT/EP2006/066127
§ 371 (c)(1),
(2), (4) Date: Mar. 7, 2008

(87) PCT Pub. No.: WO2007/028817
PCT Pub. Date: Mar. 15, 2007

(65) Prior Publication Data
US 2008/0298427 A1 Dec. 4, 2008

(30) Foreign Application Priority Data
Sep. 9, 2005 (DE) .................. 10 2005 043 037

(51) Int. Cl.
*G01K 11/26* (2006.01)
(52) U.S. Cl. ...................................................... 374/117
(58) Field of Classification Search .............. 310/346, 310/312, 315, 341; 374/117–119, 163, 183, 374/164, 141; 333/187, 234; 324/633; 73/54.24, 73/41, 64.43, 61.79
See application file for complete search history.

(56) References Cited

U.S. PATENT DOCUMENTS

| | | | | |
|---|---|---|---|---|
| 4,783,987 A | * | 11/1988 | Hager et al. | 73/32 A |
| 5,587,620 A | * | 12/1996 | Ruby et al. | 310/346 |
| 5,747,857 A | * | 5/1998 | Eda et al. | 257/416 |
| 5,873,153 A | | 2/1999 | Ruby et al. | |
| 6,300,706 B1 | | 10/2001 | Grudkowski et al. | |
| 6,684,683 B2 | * | 2/2004 | Potyrailo et al. | 73/24.06 |

(Continued)

FOREIGN PATENT DOCUMENTS

DE 196 44 290 A1 5/1998
(Continued)

OTHER PUBLICATIONS

Lee et al., "Thermally Driven Thin Film Bulk Acoustic Resonator Voltage Controlled Oscillators Integrated with Microheater Elements," Jap. J. of Appl. Phys., vol. 43, No. 1A/B, pp. L85-L87 (Jan. 15, 2004).

(Continued)

*Primary Examiner* — Gail Verbitsky
(74) *Attorney, Agent, or Firm* — Young & Thompson (57) ABSTRACT

The invention relates to a device (31) which comprises at least one piezoacoustic resonator element (2) having a piezoelectric layer (32) and two electrodes that are electrically contacted to the piezoelectric layer (32). The piezoacoustic resonator element (2) is configured in such a manner that, when a voltage is applied to the piezoelectric layer (32), a thickness oscillation of the piezoelectric layer (32) is excited via the electrodes with a resonant frequency. The inventive device is characterized by comprising, integrated into the piezoacoustic resonator element (2), a temperature measurement device (3) having a measuring element (37) that is configured as a thin layer.

13 Claims, 3 Drawing Sheets

U.S. PATENT DOCUMENTS

| | | |
|---|---|---|
| 7,104,117 B2 | 9/2006 | Büttgenbach et al. |
| 7,196,405 B1 * | 3/2007 | Ferreiro et al. ............... 257/678 |
| 7,468,608 B2 * | 12/2008 | Feucht et al. ................. 324/633 |
| 2004/0250606 A1 | 12/2004 | Buttgenbach et al. |
| 2006/0125489 A1 | 6/2006 | Feucht et al. |
| 2010/0134209 A1 * | 6/2010 | Gabl ............................ 333/187 |

FOREIGN PATENT DOCUMENTS

| | | |
|---|---|---|
| DE | 101 52 777 A1 | 5/2003 |
| DE | 102005024636 B3 * | 10/2006 |
| DE | 102006004449 A1 * | 8/2007 |
| WO | 2004/017063 A2 | 2/2004 |
| WO | 2005/052554 A1 | 6/2005 |

OTHER PUBLICATIONS

Ferrari et al., "Multisensor Array of Mass Microbalances for Chemical Detection based on Resonant Piezo-layers of Screen-printed PZT," Sensors and Actuators B, vol. 68, No. 1-3,. pp. 81-87 (Aug. 25, 2000).

Dubois, "Thin Film Bulk Acoustic Wave Resonators: A Technology Overview," MEMSWAVE 03 (Jul. 2-4, 2003).

Lakin et al., "Temperature Coefficient and Ageing of BAW Composite Materials," 2001 IEEE Int'l Freq. Control Symp. and PDA Exhib., pp. 605-608 (2001).

Lakin et al., "Thin Film Resonator Technology," IEEE 2003, RCS-IFTF Paper We1A-4, pp. 1-14 (May 5-8, 2003).

* cited by examiner

DEVICE COMPRISING A PIEZOELECTRIC RESONATOR ELEMENT, METHOD FOR PRODUCING THE SAME AND METHOD FOR OUTPUTTING A SIGNAL DEPENDING ON A RESONANT FREQUENCY

Device comprising a piezoacoustic resonator element, method for producing the same and method for outputting a signal depending on a resonant frequency The invention relates to a device comprising at least one piezoacoustic resonator element having a piezoelectric layer and two electrodes that are adjacent to the piezoelectric layer, whereby the piezoacoustic resonator element is configured in such a manner that, when an alternating voltage is applied to the piezoelectric layer, a bulk oscillation of the piezoelectric layer is induced with a resonant frequency by way of the electrodes, a method for producing such a device and a method for outputting a signal depending on a resonant frequency.

Piezoacoustic resonator elements of this type, in which a bulk wave, in other words a body volume wave, of the piezoelectric layer is induced with a resonant frequency through application of an alternating voltage field, have become known by the designation "bulk acoustic wave (BAW) piezoelectric resonator" and were developed in the first instance for high-frequency applications in communications electronics.

The most simple configuration for implementing a BAW resonator is a layer consisting of a piezoelectric material which, given suitable crystallographic orientation, for example with the c-axis perpendicular to the electrode surface, is arranged sandwiched between two electrodes.

Figure 1A:
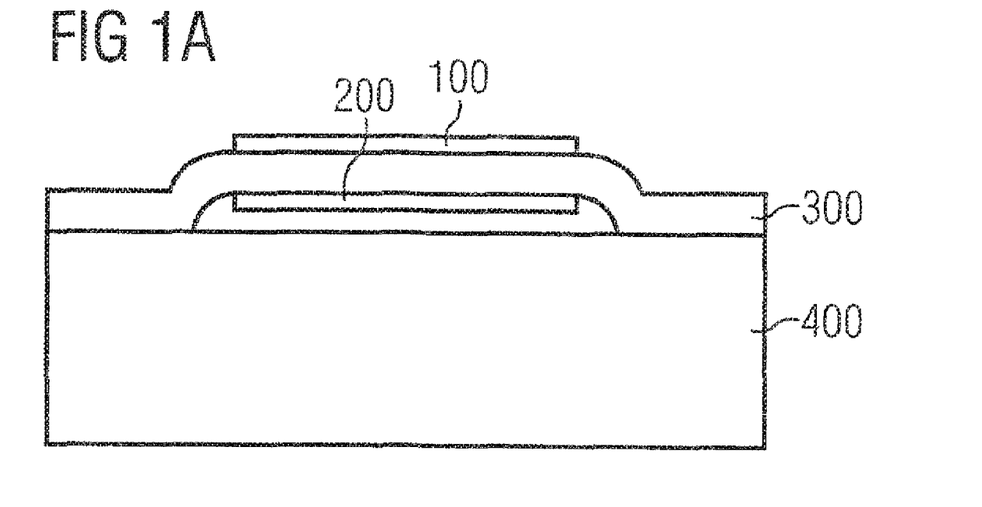
FIGS. 1A and B schematically illustrate in cross-section the structure of an FBAR and an SMR resonator as examples of BAW resonators, which are known from the prior art.
Figure 1B:
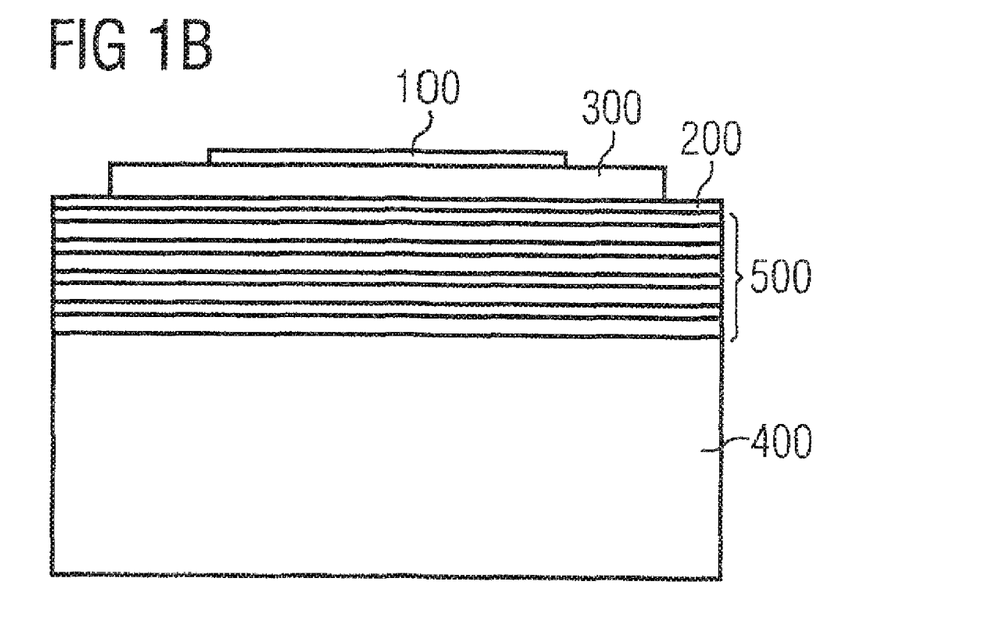

FIGS. 1 and 2 schematically illustrate two basic types of BAW resonators, as they are shown in the review article by M. Dubois "Thin film bulk acoustic resonators: a technology overview", published on the occasion of the MEMSWAVE 03 Conference, Toulouse, France, Jul. 2-4, 2003.

In this situation, FIG. 1A shows an example of a so-called "thin film bulk acoustic resonator" (FBAR) in schematic form. A piezoelectric AlN layer 300 is applied on a carrier substrate in the form of a Si wafer 400. Electrodes 100 and 200 are affixed on the underside and the upper side of the piezoelectric layer. If an electrical alternating field is applied to the piezoelectric layer 300 through the electrodes 100/200, then a conversion of the electrical energy into mechanical energy occurs as a result of the inverse piezoelectric effect. The resulting bulk acoustic wave is propagated inside the piezoelectric layer, whereby the direction of propagation is parallel to the electrical field and the wave is reflected at the electrode/air interface. The resonance oscillation is achieved when the thickness of the layer structure of the resonator is equal to half the wavelength of the input signal. In order to avoid acoustic losses into the carrier substrate a cavity is provided on the underside of the piezoelectric layer such that the acoustic waves can be reflected at the electrode/air interface.

FIG. 1B shows a structure of a BAW resonator as a so-called solidly mounted resonator (SMR). Unlike the structure shown in FIG. 1, in order to avoid acoustic losses in the direction of the carrier substrate an acoustic mirror (Bragg reflector) 500 is provided here between the lower electrode 300 and the substrate 400. This acoustic mirror comprises a plurality of layers having widely differing acoustic impedances, which are arranged in alternating sequence, for example layers of $W/SiO_2$ or Al/AlN, etc. The layer thickness is $\lambda/4$.

Compared with the so-called "surface acoustic wave" (SAW) resonators, which have already found application as filter elements in high-frequency technology for some considerable time, a basic difference consists in the fact that in the case of the BAW resonators a bulk wave (bulk oscillation) of the piezoelectric layer is induced, in contrast to surface waves in the case of surface acoustic wave resonators. The induction of a bulk wave (body volume wave) is effected by means of a suitable electrode arrangement in combination with a suitable crystallographic orientation of the piezoelectric layer. Depending on the configuration, the induced bulk oscillation of the piezoacoustic resonator element can be a longitudinal oscillation or a bulk shear wave.

This basic difference between surface acoustic wave resonators (SAW resonators) and bulk acoustic wave resonators (BAW resonators) has important consequences for the electrical properties of the components, depending on the field of application. For example, when BAW resonators are used as a filter element in the high-frequency range as a result of the electrical field generated between the two electrodes there is only minimal coupling with electrical fields outside the metal surfaces. Moreover, FBAR and BAW filters exhibit lower electrical losses in the pass band than OFW filters and are furthermore considerably more power-compatible than the latter.

Special advantages also result in respect of the manufacturing technology because BAW resonators can be integrated in a simple manner using standard IC technologies (for example CMOS, BiC-MOS, etc.) on a semiconductor chip as the carrier substrate.

In principle, however, both thick film technology, which is based essentially on screen printing techniques and is particularly suitable for structures in the range of >100 μm, and also thin film technology, such as for example physical vapor deposition using CVD/PVD methods, come into consideration as the manufacturing technology for BAW resonators.

As a result of the fact that structures in the order of magnitude considerably below 10 μm through into the sub-μm range are accessible through thin film technology, this lends itself particularly with respect to the demands for increasing integration and the advancing miniaturization of the different components.

For example, in the publication by Marc-Alexandre Dubois cited in the introduction, Thin film bulk acoustic resonators: a technology overview, MEMSWAVE 03, Toulouse, France, Jul. 2-4, 2003, reactive sputtering as the manufacturing technology for BAW resonators is described as the manufacturing process for growing aluminum nitride layers as the piezoelectric layer on suitable electrodes. It is thus possible, as described in this publication, to produce a 1.8 μm thick AlN layer having a piezoelectric coefficient of $d_{33,f}$ of 5.3±0.22 pm/V by means of reactive sputtering, which indicates the high quality of the AlN layer produced by the sputtering process.

Other than AlN, it is also possible in principle to use ZnO, PZT (lead zirconate titanate) or lithium niobate for example as the piezoelectric layer, whereby AlN however exhibits advantages with regard to its chemical, electrical and mechanical properties, particularly as far as the previously mentioned integration on a semiconductor chip is also concerned however.

As mentioned in the introduction, BAW resonators were originally developed as passive components for use in high-frequency technology particularly for systems in the target range of 1 to 10 GHz. The production of voltage controlled oscillators (VCO) or of amplifiers (low noise amplifier, LNA) can in particular be cited as examples of use.

In addition to the use as components for high frequency technology, the use of a BAW resonator as a sensor has been proposed. For example, the application WO 2004/017063 A2 from the applicant describes a sensor for ascertaining the sorption of a particular substance on the surface of the BAW resonator. The substance in question can be identified in this manner. In this situation, sorption can mean adsorption and/or absorption.

Structurally, to this end the resonator has a sensitive coating, for example in the form of a polymer film, which is applied on an electrode of the resonator. Different substances to be detected, hydrocarbons for example, can be absorbed on this polymer film. The substance to be detected is present in a fluid (gas or liquid) which serves as the measuring medium. For measurement purposes the sensor is brought into contact with the measuring medium which contains the substance that can be sorbed on the sensitive coating. Normally, a microfluidics system with a measuring cell is used, through which the measuring medium flows over the relevant surface section of the sensor.

The surface section of the sensor on which the substance in question is sorbed is based in many cases on the type of the substance to be detected in order in this manner to be able to detect a particular substance selectively from a mixture of a plurality of substances. For example, the aforementioned patent application describes the detection of DNA fragments by means of a sensor which has a coating with a selected DNA sequence on a surface section of the electrode which makes possible a sorption of suitable DNA sequences in accordance with the lock-and-key principle.

With regard to the detection of DNA, it is crucial to be able to differentiate strands with single- or multibase mismatches compared with a perfect match (complementary strand). This depends crucially on the equilibrium of the desorption of the DNA strands on the surface section. This equilibrium of the desorption is determined by the circumstances of the corresponding system, such as for example the type of coating, concentration of the species involved, temperature etc.

As a result of the sorption of a substance on the resonator, the resonant frequency changes depending on the mass of the sorbed substance. By measuring the resonant frequency it is therefore possible to deduce the sorption of a substance. The characteristic value concerned is the mass sensitivity of the resonator, which is proportional to the square of the resonant frequency of the resonator.

In the aforementioned patent application, the positive influence of an extremely small layer thickness of the piezoelectric layer in the range from 0.1 µm to 20 µm is described, which has a positive effect on the sensitivity of detection of the sensor as a result of said relationship between mass sensitivity and resonant frequency. In addition, advantages result in respect of integration density and miniaturization, particularly with regard to sensor arrays which contain a plurality of such sensor elements.

Since the resonant frequency of the piezoacoustic resonator is temperature-dependent within certain limits, the signal output by a filter or sensor with a BAW resonator may be subject to an undesired temperature dependency. In order to solve this problem, it has been proposed that different materials having positive and negative temperature coefficients in the form of a composite be used in order by this means to equalize the temperature drift through compensation. This solution approach is described for example in the publication by K. M. Lakin, K. T. McCarron, J. F. McDonald and J. Belsick, "Temperature Coefficient and Aging of BAW Composite Materials", 2001, Frequency Control Symp. Proc., pp. 605-608.

In the publication by K. M. Lakin, Thin Film Resonator Technology, IEEE 2003, FCS-IFTF Paper We1A, May 5-8, 2003, a resonator compensated in respect of the temperature response is described, in which AlN is used as the piezoelectric layer and $SiO_2$ is used for the compensation. As a result of the positive temperature coefficient for $SiO_2$ of +85 ppm/° C. in comparison with −25 ppm/° C. for AlN, a compensation of the temperature drift can be achieved by successively increasing the proportion of $SiO_2$.

This solution approach does however have inherent disadvantages because it involves restrictions in respect of the composition of the materials to be used or the overall structure of the element.

The object of the invention is to set down an improved device comprising at least one piezoacoustic resonator element of the type mentioned in the introduction which solves the problem of the temperature dependency of the resonant frequency, and also a simple and cost-effective method for manufacturing such a device. In particular, an object of the present invention is to provide a device of such a type that is designed as a sensor for the detection of a substance, with enhanced accuracy of measurement and expanded field of application.

Furthermore, an object of the invention is to set down an optimized method for outputting a signal depending on a resonant frequency of a piezoacoustic resonator.

This object is achieved by a device with a piezoacoustic resonator element having the features described in claims and a manufacturing method having the features described in claims. An optimized method for outputting a signal depending on a resonant frequency of a piezoacoustic resonator is set down in claims.

According to the invention, a temperature measuring device (3) designed to be integrated into the piezoacoustic resonator element is provided which is used to measure the operating temperature of the device.

The operating temperature of the device for the purpose of the present invention can be the temperature of the piezoacoustic resonator element. The invention is not however restricted thereto. The location of the operating temperature of the device can be any desired section of the device itself and/or a surrounding section in the vicinity of the device.

In particular, when configuring the device as a sensor for the detection of a substance the operating temperature can relate to the surface section on which the substance to be detected is sorbing. The temperature of the measuring medium in which the substance is situated can also constitute an operating temperature of the device for the purpose of the present invention.

For the purpose of integrating the temperature measuring device into the piezoacoustic resonator element the measuring element of the temperature measuring device is advantageously implemented as a layer. With regard to a preferred embodiment, the layer can essentially consist of a material which can be implemented as a resistance heater in order to additionally heat the device.

The layer thickness of the temperature element advantageously lies in the range below 25 µm, by particular preference the layer thickness is <10 µm, and by greatest preference the layer thickness is <1 µm. A small layer thickness benefits the integration of the heating element into the piezoacoustic resonator element through the use of thin film technology methods, such as for example deposition methods using PVD/CVD processes. By this means, it becomes possible in a particularly simple manner to process the temperature measuring device jointly with the piezoacoustic resonator element implemented in layer technology.

With regard to one simple embodiment of the device according to the invention the temperature measuring device implemented as a layer is implemented together with the piezoacoustic resonator element on a carrier substrate, which can be a semiconductor substrate.

In this situation, intermediate layers can be arranged between the measuring element layer and the carrier substrate. For example, the piezoacoustic resonator element and the measuring element can be arranged in layer technology on intermediate layers which act as an acoustic mirror (Bragg reflector) that is intended to reduce an acoustic loss in the direction of the substrate.

With regard to a particularly simple and advantageous embodiment, the carrier substrate is implemented as a membrane which for example can be manufactured by means of rear-side etching of a semiconductor substrate with a $SiO_2$ or $Si_3N_4$ layer as the etch stop. Alternatively, the membrane can cover a hollow space in the carrier substrate, in other words be implemented as a surface micromachined feature, as shown in FIG. 1A for example.

In addition to the measuring element, the temperature measuring device can include normal function elements such as means for connection to an external voltage supply for example.

By preference, the distance between the measuring element and the piezoelectric layer of the piezoacoustic resonator is less than 250 μm, by greater preference less than 150 μm and by greatest preference less than 50 μm. This produces a slight temperature deviation in the range of a few tenths of a Kelvin or less.

In principle, according to the invention an electrode of the piezoacoustic resonator element itself can act as a temperature measuring element.

The measuring element can be manufactured by normal thick film technology techniques. An improved integration capability and improved miniaturization results however when using, for example, thin film technologies known from semiconductor technology for manufacturing layer thicknesses in the sub-μm range right through to the nm range. These can be normal PVD/CVD methods.

As far as the material properties of the measuring element are concerned, a material is preferably used which can act as a metal resistance thermometer. In this case the measuring element can also be operated as a heating element, whereby the device is not only set up to ascertain the temperature from the resistance value of the temperature measuring element but is also to control the temperature of the device by heating up. In this context, platinum in particular, whose temperature coefficient of resistance is $3.85 \cdot 10^{-3}/°$ C., should be mentioned with regard to a range of application from −200 to +850° C. Nickel can also be used if the temperature to be measured does not exceed 150° C. Nickel offers advantages over platinum particularly in respect of its lower price.

Configuring the device with a temperature measuring device (microsensor) and heating facility in one component makes possible a closed temperature regulation of the operating temperature of the piezoacoustic resonator element which comprises control of the temperature by the heating facility, measurement by the temperature measuring device of the operating temperature obtained and subsequent regulation of the operating temperature depending on the temperature measured.

In this manner, it is for example possible to carry out an effective temperature compensation of the resonant frequency by ensuring that the device is being operated at a predefined temperature.

The device according to the invention, in which a temperature sensor is implemented integrated with the piezoacoustic resonator element, can include an evaluation facility with a memory facility in which the corresponding characteristic curve for the temperature dependency of the resistance for the given material is stored, and with a read-out facility for reading out a temperature value as a function of the measured resistance value. The evaluation facility together with the read-out facility can be part of an external facility which is connected electrically in a suitable manner to the temperature measuring device. Electrically connected in the context of the present invention can also mean a normal wireless connection and is not limited to conventional wiring.

With regard to one particularly preferred embodiment, the electronic components required for the evaluation facility are also integrated into the carrier substrate of the piezoacoustic resonator element in order to further increase the integration density. Corresponding methods and the technologies required for this purpose are basically known from the field of integration of electronic components. The evaluation facility can however also be implemented as an external device.

In addition to such an evaluation facility for determining the temperature from the measured value provided by the temperature measuring device, it is possible to integrate a further evaluation facility for determining the resonant frequency of the resonator in the piezoacoustic resonator element. This can be a case for example of a high-frequency circuit in which the resonator determines the frequency. Such an evaluation facility for ascertaining the resonant frequency can be integrated in a semiconductor substrate in a known manner for example by using CMOS, bipolar or BIC-MOS technology.

The device can additionally include a correction facility for correcting the output signal from the piezoacoustic resonator element as a function of the temperature ascertained. To this end, the temperature response of the resonant frequency of the piezoacoustic resonator element can be stored as a characteristic curve in the corresponding device. With regard to the correction facility, this can also be an integrated or an external component.

Special advantages result for the case of the embodiment of the device according to the invention as a sensor for the detection of a substance, since by controlling the temperature it is possible to specifically control the equilibrium conditions for the sorption of the substance to be detected on the surface section of the piezoacoustic resonator element. In this manner, depending on the substance to be detected, the accuracy of the measured value acquisition can be increased. At the same time, the field of application of the sensor can be expanded because the sorption conditions, which in addition to the temperature are determined by the measuring medium (gas, liquid), by the substance to be detected, and also by further substances which may be present in the measuring medium, can be specifically set. In this manner, detection becomes available for substances which for example only sorb on the surface section of the sensor at a predefined temperature. In this situation, "detection of a substance" can be used for the identification of a substance in the context of the present invention. However, the sensor can also be implemented as a mass sensor for ascertaining a sorbed quantity.

With regard to the configuration as a sensor for the detection of a substance it can be advantageous for the temperature measuring device to be situated at a position of the sensor element which ensures that the measuring element is situated in contact with the measuring medium. By this means it is also possible for example to measure a warming of the measuring medium which for example flows through a flow cell of the sensor.

The invention also includes a manufacturing method for manufacturing a device according to the invention. With regard to this method, a carrier substrate is coated with a metallic layer. An electrode of the piezoacoustic resonator element and the measuring element are created by means of subsequent microstructuring of this metallic layer. In this situation, the important aspect is the fact that by microstructuring only one metallic layer in one work process, one part of the piezoacoustic resonator element and the measuring element can be produced. Particularly suitable for microstructuring purposes are photolithographic methods, such as are known in principle from semiconductor technology.

The method according to the invention makes possible a considerable rationalization of the manufacturing process because the additional resource requirement is extremely low and is essentially limited to an adaptation of the layout.

With regard to one particularly advantageous embodiment, platinum is applied to the substrate for example by means of physical vapor deposition. Platinum is also suitable as a resistance thermometer on account of its temperature dependency of the resistance, with the result that an electrode of the resonator element, a heating element of the heating facility and a measuring element of a temperature measuring device can be manufactured in one method step by microstructuring the applied layer.

In this situation all three function elements, heating element, measuring element and electrode, can be implemented by the same layer section which is controlled differently.

The resonator and the measuring element can be brought into contact by way of the carrier substrate with a passive high-frequency component, for example an LTCC (low temperature cofired ceramics) substrate, through bond pads using flip chip technology, such that a module is produced. This serves to improve the electrical properties of the high-frequency component because inductances of corresponding connecting wires can be avoided. In addition, flip chip technology makes it possible to achieve an increased packing density for the different components and thus contributes substantially to the improved integration and miniaturization in the production of complete HF modules.

The invention also includes a method for outputting a signal which depends on a resonant frequency, comprising the steps: Detection of the operating temperature of a piezoacoustic resonator element of a device comprising at least one piezoacoustic resonator element having a piezoelectric layer and two electrodes in electrical contact with the piezoelectric layer, whereby the piezoacoustic resonator element is configured in such a manner that when an alternating voltage is applied to the piezoelectric layer by way of the electrodes a bulk acoustic wave of the piezoelectric layer is induced with a resonant frequency, through a measuring element.

Induction of a bulk oscillation of the piezoelectric layer of the piezoacoustic resonator element with a resonant frequency, and Outputting of an output signal as a function of the measured temperature.

With regard to a particularly advantageous embodiment of the method according to the invention, this is concerned with a method for detecting a substance, which is preferably carried out using the device according to the invention. This method comprises the steps:

Bringing together the fluid and the piezoacoustic resonator in such a manner that the substance can be absorbed and/or adsorbed at one section of the resonator, and Determining a resonant frequency of the resonator, whereby the quantity of the substance sorbed on the surface section can be deduced from the resonant frequency. With regard to the method according to the invention, before the step in which the resonant frequency is determined the operating temperature of the device with the piezoacoustic resonator element is detected.

With regard to the method according to the invention, the operating temperature of the device can in addition advantageously be controlled with an appropriate piezoacoustic resonator element. This is done in a particularly simple manner by means of the device described above, in which a temperature measuring element and a heating element are simultaneously integrated in the device. In this situation, the method can include the step of regulating the operating temperature, in other words control as a function of the measured temperature.

In this manner, depending on the substance to be detected, the accuracy of the sensor can be significantly increased. Moreover, the method makes it possible to detect certain substances which for example cannot be detected at room temperature.

The present invention yields the following advantages in particular:

As a result of a low additional resource requirement and processing a further necessary element can be integrated with the measuring element on the carrier substrate (chip).

This takes account above all of the integration, particularly in the case of heavily miniaturized systems.

In contrast to a discrete solution, the measuring element can be brought very close to the piezoacoustic resonator, such that an appropriate accuracy of measurement results.

Particularly when platinum is used, a heating element can be provided at the same time. This makes possible a complete temperature regulation capability.

By detecting the operating temperature of the piezoacoustic resonator element it is possible to take account of the temperature response of the resonant frequency.

The invention creates piezoacoustic resonators which have a simple structure and, compared with the previously known BAW resonators, deliver output signals which are fully discriminated with reference to the background signal that results from the change in temperature of the device. The temperature information required for this in the immediate vicinity of the resonator element under operating conditions is made available by the temperature measuring device which is arranged in the immediate vicinity of the resonator element. This is implemented by integrating the piezoacoustic resonator element with the temperature measuring device by utilizing fundamentally known technologies, such as are known for example from thin film technology and/or thick film technology.

In this manner, a cost-effective device comprising a piezoacoustic resonator element can be made available which can be used for example as a filter element for HF applications, as a sensor (biosensor) or as an actuator element (mixing, pumping). In addition to the piezoacoustic resonator element with the temperature measuring device, the device according to the invention can include different types of evaluation facilities for ascertaining the temperature from the measured value delivered by the temperature measuring device and/or an evaluation facility for determining a resonant frequency. A correction facility can additionally be provided which makes it possible, on the basis of a predefined characteristic, to carry out a correction of the initial value for the device with respect to the temperature given in the respective operating situation. In this manner, the accuracy of the device compared with conventionally known devices of said type can be significantly improved.

Advantageous embodiments and further details of the present invention will be described in the following with reference to different embodiments with reference to the figures.

FIG. 4 shows a flowchart of an embodiment of a method for manufacturing the device according to the invention.

Figure 2:
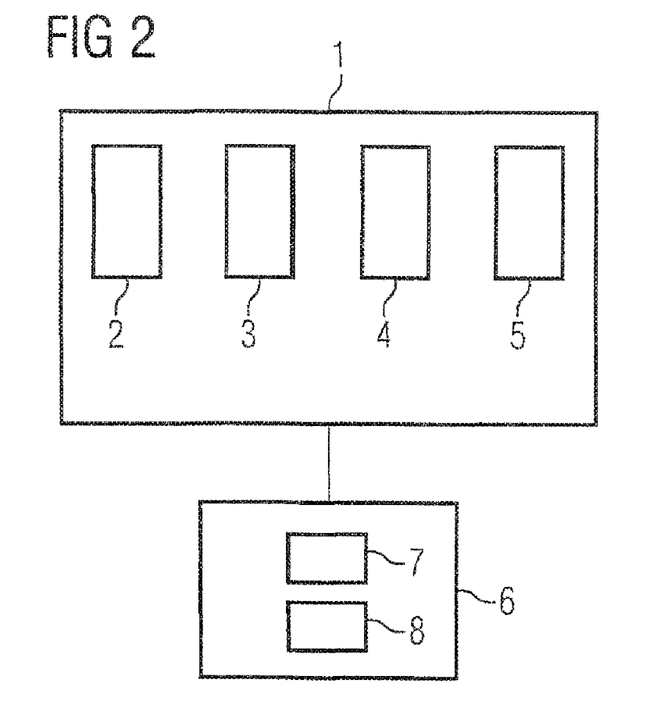
FIG. 2 schematically illustrates the structure of a first embodiment of a device according to the invention.

FIG. 2 schematically illustrates the structure of an embodiment of the device according to the invention. According to this, the device 1 according to the invention comprises a piezoacoustic resonator element 2, a temperature measuring device 3, an evaluation facility 4 for determining the resonant frequency of the piezoacoustic resonator element 2 and an evaluation facility 5 for determining the temperature from a measured value which is made available by the temperature measuring device 3. In this situation in the present embodiment this is the resistance of the temperature measuring device 3.

The invention is not restricted to this, however. In fact, any desired temperature sensors known from the prior art or similar facilities for measuring the temperature can be used, insofar as they can be integrated with the piezoacoustic resonator element in terms of process engineering.

Whereas in the embodiment illustrated in FIG. 2 the evaluation facility 4 for determining the resonant frequency has been shown as being integrated into the device 1, the invention is not restricted to this embodiment. In fact, the evaluation facility for determining the resonant frequency can also be provided as an external device with which the device 1 is connected electrically. The evaluation facility 5 for determining the temperature can also, even though it is shown as an integral component of the device 1 in the case of the present embodiment, be provided externally.

For example, with regard to a simple and advantageous embodiment of the device according to the invention the evaluation facility 5 for determining the temperature can be provided as an external memory facility in which the temperature response of the resistance of the temperature measuring device 3 is stored. The temperature can then be deduced from the resistance value of the temperature measuring device by means of this facility.

The basic components of both evaluation facilities 4 and 5 are based on the particular instance of use (frequency, temperature, etc.) and are already known as electronics components.

The device 1 is connected to a device 6 for correcting the resonant frequency as a function of the ascertained temperature. The correction device 6 is implemented as an external device and includes a storage element 7, in which the temperature response of the resonant frequency is stored. Furthermore, the correction device 6 includes a facility 8 for correcting the resonant frequency on the basis of the values stored in the storage element 7. To this end the correction facility 8 is set up to output this corrected resonant frequency as an output value.

Figure 3:
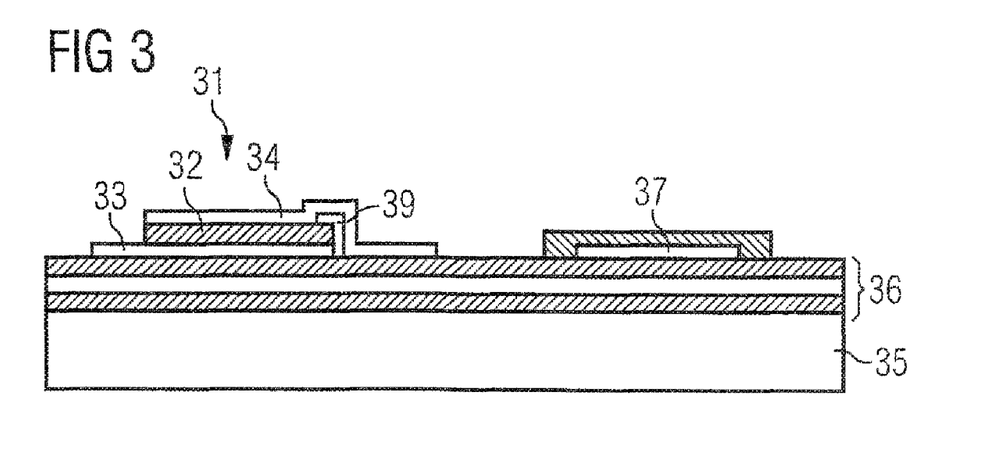
FIG. 3 shows an embodiment in cross-section of a piezoacoustic resonator element and a temperature measuring device, which are integrated on a carrier substrate.

FIG. 3 schematically illustrates the structure of a device 30 according to the invention, in which a piezoacoustic resonator element and a temperature sensor are implemented integrated together on a carrier substrate. The piezoacoustic resonator 31 comprises a piezoelectric layer 32 consisting of ZnO, a first platinum electrode 33 on its underside and a second platinum electrode 34 on its upper side. The lower platinum electrode 33 is accommodated on a silicon carrier substrate 35. An acoustic mirror 36, which is intended to prevent acoustic losses in the direction of the substrate 35, is provided between the piezoacoustic resonator element 31 and the carrier substrate 35.

The thickness of the Pt electrodes 33, 34 lies in the region of 250 nm. The thickness of the piezoelectric layer (ZnO) is 400 nm. The array shown in FIG. 3 was manufactured using photolithographic methods for structuring a platinum-coated Si wafer.

A temperature measuring device is accommodated together with the piezoacoustic resonator 31 on the semiconductor substrate 35. The temperature measuring device has a layer 37 consisting of platinum having a layer thickness of 1 μm, which serves as the measuring element of the temperature measuring device. The platinum layer 37 is insulated from the piezoacoustic resonator 31 by means of the insulation 38 which consists of $Al_2O_3$.

An embodiment of a method for manufacturing the device according to the invention is described in the following with reference to FIG. 4.

In step 41, an Si wafer element whose top layer consists of silicon oxide ($Si_xO_y/SiO_2$) is provided with a Pt layer by means of sputtering.

In step 42, an electrode for the piezoacoustic resonator and also a temperature measuring element are produced by microstructuring.

The remaining steps 43 for constructing a BAW resonator are basically known from the prior art and do not therefore require any detailed discussion at this point. For example, a membrane on which the resonator element and the temperature measuring device are arranged can be produced by means of rear-side etching of a substrate. Further method steps comprise the deposition of a piezoelectric layer, the application of the second electrode and also the corresponding contacting of the elements in order to produce the device.

As already mentioned, it is particularly advantageous to create the lower or the upper electrode and also the measuring element by microstructuring the same Pt layer. In this manner it is possible to create not only the electrode and measuring element from one layer, but for example also a heating element of a heating facility. With regard to a particularly advantageous embodiment, electrode, heating element and measuring element of the temperature sensor can however also be formed from a layer section which is controlled differently according to the desired function.

Figure 5:
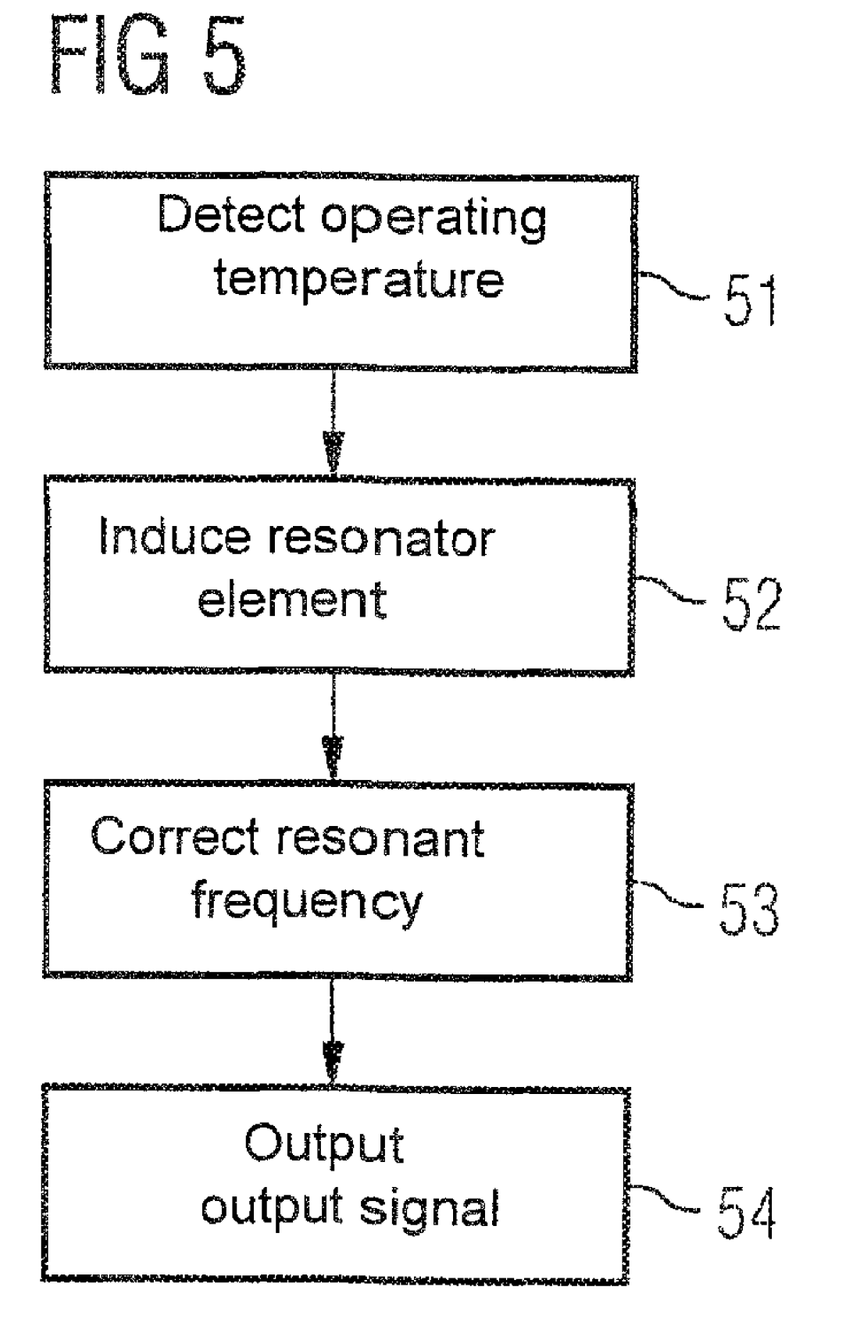
FIG. 5 shows a flowchart of an embodiment of a method according to the invention for outputting a signal value which depends on a resonant frequency.

Referring to FIG. 5, an embodiment of a method for outputting a signal which is dependent on a resonant frequency is described.

In step 51, an operating temperature of a device with a piezoacoustic resonator element is detected with a temperature measuring device.

In step 52, a bulk wave (in other words, bulk oscillation) is induced with a resonant frequency by applying an alternating voltage to the electrodes of the piezoelectric layer of the piezoacoustic resonator element.

In step 53, a correction of the measured resonant frequency is carried out as a function of the measured temperature.

In step 54, an output signal is output as a function of the corrected value.

Such a method according to the invention is particularly expedient when it is configured as a method for the detection of a substance. In this situation, it comprises the additional steps of bringing together a surface section of the piezoacoustic resonator set up for sorption of a substance with a fluid which contains the substance in question to be detected. After the substance has sorbed, the resonant frequency which depends on the mass of the sorbed substance is measured. In this situation, the measurement in question can be differential, in other words a measurement of the resonant frequency before and after sorption of the substance. From the measured resonant frequency it is possible to deduce the sorption of the substance in question in the fluid. By detecting the operating temperature of the device it is possible to carry out the determination of a selective sorption of a particular substance which sorbs only at a predefined temperature. This embodiment includes the method step for evaluating the measured resonant frequency for the purpose of detecting the substance in question and outputting a relevant output value.

The individual structural features of the embodiments described above can be combined with one another in any desired manner in order to provide further forms of embodiment which are optimized for the corresponding application situation. Insofar as such modifications are obvious without further ado to the person skilled in the art, they are intended to be implicitly disclosed by the description of the above embodiments without itemizing all combinations in detail.

The invention claimed is:

1. A device comprising:
at least one piezoacoustic resonator element (2) having a piezoelectric layer (32); and
two electrodes that are contacted electrically with the piezoelectric layer (32),
wherein the piezoacoustic resonator element (2) is configured in such a manner that, upon voltage being applied to the piezoelectric layer (32), a bulk acoustic wave of the piezoelectric layer (32) is induced with a resonant frequency by way of the electrodes,
further comprising a temperature measuring device (3) implemented to be integrated with the piezoacoustic resonator element (2) being present, which includes a measuring element implemented using thin film technology,
the temperature measuring device (3) and the piezoacoustic resonator element (2) being embodied using thin film technology (Fn) on a common carrier substrate (35) and an electrode of the resonator element (2) and the temperature measuring device (3) being arranged as layers on the carrier substrate (35), with
a layer thickness of the temperature measuring device amounting <25 μm and the device being configured as a sensor element for detecting a substance with a piezoacoustic resonator element (2), whereby the piezoacoustic resonator element (2) has a surface section for sorption of the substance and the output signal from the resonator element (2) is dependent on the sorption of the substance, with an acoustic mirror (36) being arranged between the piezoacoustic resonator element (31) and the carrier substrate (35), in order to amplify the acoustic signal,
the temperature measuring device (3) being positioned at such a position of the sensor element that the temperature measuring device (3) is in contact with a measuring medium during the measuring process of the sensor element, in which the substance to be detected is located, and that the measuring element, the temperature measuring device (3) and also a heating element of the heating facility can be operated, with an external evaluation device (4) or evaluation device implemented to be integrated in the device being provided to determine the temperature from the change in resistance of the measuring element as a function of the temperature, by means of which the balance conditions of the sorption of the substance to be detected on the surface section of the piezoacoustic resonator element (2) are targetedly controlled by controlling the temperature.

2. The device as claimed in claim 1, wherein the carrier substrate (35) consists of a semiconductor material.

3. The device as claimed in claim 1, wherein the measuring element is implemented as a metallic conductor.

4. The device as claimed in claim 1, wherein the measuring element essentially consists of platinum.

5. The device as claimed in claim 1, wherein an acoustic mirror (36) comprising a plurality of layers is arranged between the carrier substrate (35) and the piezoacoustic resonator element (2).

6. The device as claimed in claim 1, further comprising: a the heating element and the piezoelectric layer (32) are separated by less than 100 μm.

7. The device as claimed in claim 1, wherein the piezoacoustic resonator element (2) is implemented as an array, comprising a plurality of piezoelectric layers (32) with corresponding electrodes and at least one temperature measuring device (3).

8. The device as claimed in claim 1, further comprising:
a heating facility implemented so as to be integrated with the piezoacoustic resonator element (2).

9. The device as claimed in claim 1, further comprising:
a correction facility (8) for correcting the resonant frequency of the piezoacoustic resonator element (2) on the basis of the value detected by the temperature measuring device (3).

10. The method for outputting a signal which depends on a resonant frequency, comprising:
detecting the operating temperature of a piezoacoustic resonator element (2) of the device as claimed in claim 1, by a temperature measuring device (3),
exciting a volume oscillation of the piezoelectric layer (32) of the piezoacoustic resonator element (2) with resonance frequency,
outputting an output signal as a function of the measured operating temperature.

11. The method as claimed in claim 10, further comprising:
outputting an output value as a function of the measured resonant frequency.

12. The method as claimed in claim 10, the method further comprising:
detecting a substance comprising the steps of:
bringing together a surface section of the piezoacoustic resonator (31) set up for the sorption of the substance with a fluid which contains the substance to be detected, and
measuring the resonant frequency as a function of the quantity of the accumulated substance.

13. The method as claimed in claim 10, further comprising:
controlling the operating temperature of the piezoacoustic resonator element (2).

* * * * *